United States Patent [19]
Suzuki et al.

[11] Patent Number: 4,882,030
[45] Date of Patent: Nov. 21, 1989

[54] AIR-FUEL RATIO DETECTION SYSTEM FOR ENGINE EXHAUST GAS

[75] Inventors: Seikoo Suzuki, Hitachiota; Masayuki Miki, Katsuta, both of Japan; Takao Sasayama, Tarrytown, N.Y.; Minoru Osuga; Yoshishige Oyama, both of Katsuta, Japan

[73] Assignee: Hitachi, Ltd., Tokyo, Japan

[21] Appl. No.: 239,008

[22] Filed: Aug. 30, 1988

Related U.S. Application Data

[63] Continuation of Ser. No. 891,645, Aug. 1, 1986, abandoned.

[30] Foreign Application Priority Data

Aug. 2, 1985 [JP] Japan .................. 60-169841

[51] Int. Cl.$^4$ ........................ G01N 27/46
[52] U.S. Cl. .................. 204/406; 204/425; 204/427
[58] Field of Search ........... 204/406, 424, 425, 427, 204/412, 15

[56] References Cited

U.S. PATENT DOCUMENTS

| | | | |
|---|---|---|---|
| 4,282,080 | 8/1981 | Muller et al. | 204/15 |
| 4,578,172 | 3/1986 | Yamada | 204/406 |
| 4,591,421 | 5/1986 | Yamada et al. | 204/425 |
| 4,594,139 | 6/1986 | Asayama et al. | 204/425 |
| 4,601,793 | 7/1986 | Asayama et al. | 204/425 |
| 4,626,338 | 12/1986 | Kondo et al. | 204/425 |
| 4,629,549 | 12/1986 | Kojima et al. | 204/425 |

OTHER PUBLICATIONS

SAE Technical Paper Series, "Air-Fuel Ratio Sensor for Rich, Stoichiometric and Lean Ranges", Reprint from SP-655, Sensor and Actuators (1986).

*Primary Examiner*—John F. Niebling
*Assistant Examiner*—Ben C. Hsing
*Attorney, Agent, or Firm*—Fay, Sharpe, Beall, Fagan, Minnich & McKee

[57] ABSTRACT

An air-fuel detection system comprising a solid electrolyte, first and second electrodes formed on the surface of the solid electrolyte, a diffusion resistor formed on the first electrode for controlling the gas diffusion into the first electrode, and a detector circuit for detecting conditions of the engine exhaust gas to detect the air-fuel ratio thereof, wherein the detector circuit measures the electromotive force generated between the first and second electrodes during a first period, and controls a selected one of the voltage and current applied between the first and second electrodes to keep the electromotive force constant during a second period, the selected one of the voltage and current being produced as a signal representing the air-fuel ratio.

21 Claims, 17 Drawing Sheets

EXHAUST GAS →

FIG. 3A
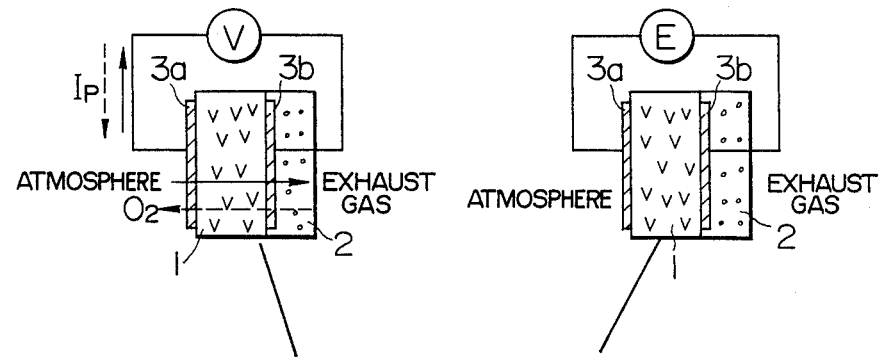
FIG. 3B
FIG. 3C
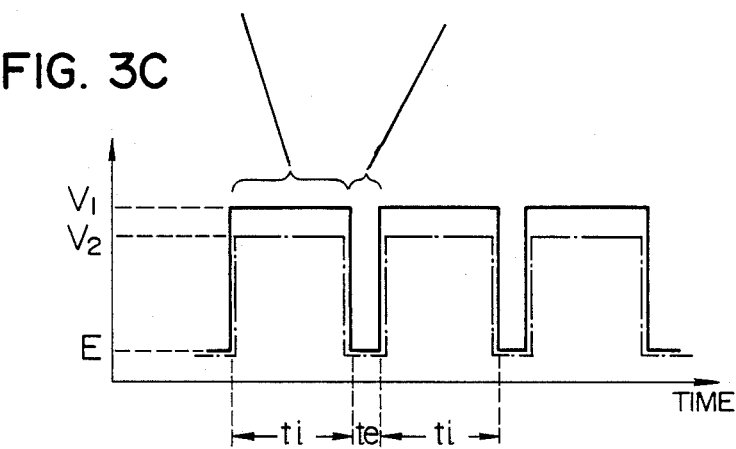

$\lambda' > \lambda > 1$ $\lambda'' < 1$ $V_P > V_{PG}$
$\lambda > 1$ $V_P < V_{PG}$
$\lambda < 1$ $\lambda > 1$   $V_{PX} > V_H > V_{PG}$ $\lambda < 1$   $V_{PX} < V_H < V_{PG}$

AIR-FUEL RATIO DETECTION SYSTEM FOR ENGINE EXHAUST GAS

This application is a continuation of application Ser. No., 891,645, filed Aug. 1, 1986 now abandoned.

BACKGROUND OF THE INVENTION

The present invention relates to an air-fuel ratio detection system, or more in particular to a detection system for detecting the air-fuel ratio of the exhaust gas of an engine.

Conventional engine air-fuel detection systems for detecting the stoichiometric air-fuel ratio are widely used to control internal combustion engines.

In recent years, an air-fuel ratio detection system for lean burn control has been under development for improving the fuel economy. As an example, the U.S. Pat. No. 4,282,080 discloses a system widely known for detecting the lean-mixture air-fuel ratio from the critical current which flows when the oxygen diffused from a diffusion resistor is fetched by a solid electrolyte cell.

In another well-known system as disclosed in the U.S. Pat. No. 4,158,166 (JP-A-78-66292), on the other hand, the carbon monoxide or the like diffused from a diffusion resistor is reacted with the oxygen collected by a solid electrolyte cell, and the rich-mixture air-fuel ratio is detected by the critical current that flows in the solid electrolyte in this process.

Nevertheless, there are no conventional systems which are capable of detecting the air-fuel ratio over a wide range from lean to rich mixtures.

SUMMARY OF THE INVENTION

The object of the present invention is to provide an air-fuel ratio detection system capable of detecting the air-fuel ratio over a wide range from lean to rich air-fuel mixtures.

According to the present invention, there is provided an air-fuel ratio detection system comprising means for measuring the electromotive force generated between the first and second electrodes made up of a solid electrolyte during a fist period, means for controlling the voltage or current applied to the first and second electrodes to attain a predetermined value of the electromotive force during a second period, and means for producing the voltage or current as a signal representing an air-fuel ratio.

BRIEF DESCRIPTION OF THE DRAWINGS

FIGS. 3A–3C, 4A–4B and 5A–5B are diagrams for explaining the operating principle of the present invention.

DESCRIPTION OF THE PREFERRED EMBODIMENTS

An embodiment of the present invention will be described below with reference to the accompanying drawings.

Figure 1:
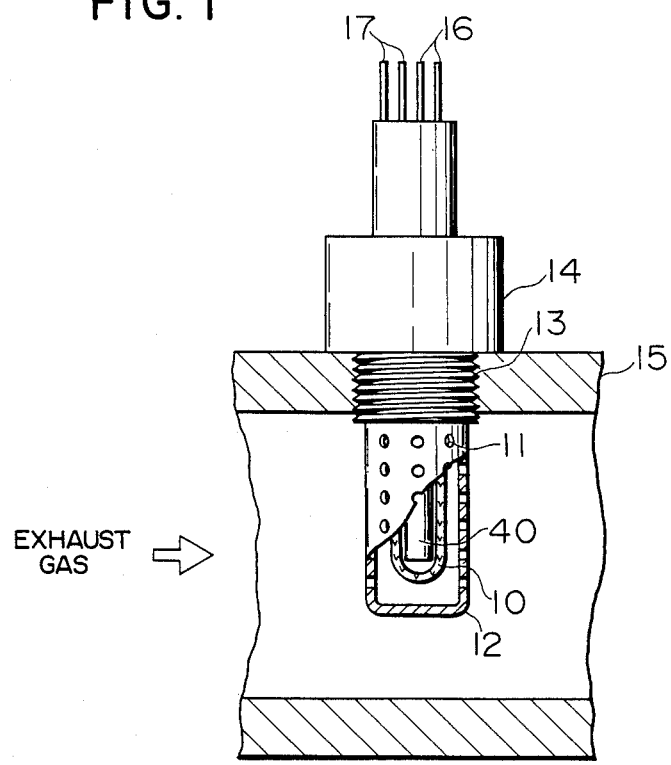
FIG. 1 is a partially cut-away sectional view showing an example of a sensor used in the present invention.

First, explanation will be made about an example of a sensor used in the present invention with reference to FIG. 1. A tubular detector 10 is arranged within a protective tube 12 having apertures 11, and secured within a plug member having a screw 13. The apertures 11 may take various shapes. This assembly is mounted on an exhaust pipe 15 in which the exhaust gas flows. Reference numeral 16 designates electrode terminals, and numeral 17 heater terminals, through which the detector is connected to an electronic circuit. The zirconia solid electrolyte 10 making up the tubular detector has mounted therein an elongate heater 40 (a W heater formed on an alumina bar) for heating the detector. The heater 40 may alternatively be located outside of the zirconia solid electrolyte 10. This heater 40 is provided for the purpose of heating the zirconia solid electrolyte of the detector to a high temperature of at least 600° C. to reduce the impedance thereof. This heater is recommended but is not absolutely necessary. The detector 10 includes electrodes (such as of platinum) on both the interior and exterior of the tubular zirconia solid electrolyte and a porous diffused resistor formed on the outer electrode. The atmospheric air is introduced into the solid electrolyte, and the exterior thereof is exposed to the exhaust gas environment.

Figure 2:
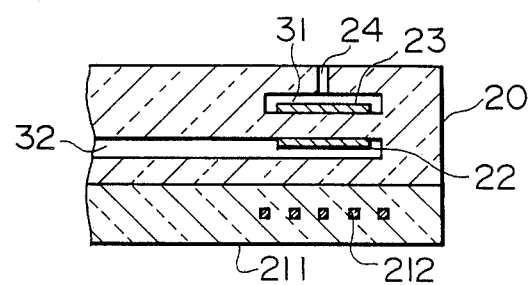
FIG. 2 is a partial sectional view showing another example of the sensor used in this invention.

Another example of the sensor used in the present invention is shown in FIG. 2. This drawing shows the case in which the zirconia solid electrolyte is tubular, and the diffused resistor has only one aperture. The atmospheric air is introduced through a path 32 in the zirconia solid electrolyte into the first electrode 22. The residual oxygen and the uncombusted gas in the exhaust gas flow by diffusion into the second electrode 23 through the porous diffusion resistor 24. The zirconia solid electrolyte 20 is controlled by being heated to a high temperature by a heater 212 in the alumina insulating layer 211 secured to the electrolyte 20.

Anyway, the zirconia solid electrolyte may basically take any form as far as it has a couple of electrodes and is so constructed that the atmospheric air is introduced into one of them, and the exhaust gas flows into the other through the diffusion resistor.

The operating principle of the present invention will be described below with reference to FIG. 3.

In FIGS. 3A and 3B, numeral 1 designates a solid electrolyte conductive of oxygen ions with platinum electrodes $3a$, $3b$ formed on both sides thereof. The electrode $3a$ is in contact with the atmosphere, and the electrode $3b$ with the exhaust gas through the porous diffusion resistor 2.

In this detection system, the operation for applying the voltage V to the solid electrolyte 1 to cause the current $I_P$ for charge and discharge of oxygen in the diffusion resistor 2 as shown in FIG. 3A, and the operation for measuring only the electromotive force E generated in the solid electrolyte 1 are performed alternately by switching circuits of these two functions in a timesharing manner. The current $I_P$ shown in FIG. 3A changes in absolute value and direction with the air-fuel ratio. This is by reason of the fact that the value of the voltage V is changed to charge and discharge the oxygen in the diffusion resistor 2 so that the electromotive force E measured during the period shown in FIG. 3B may The terminal voltage of the electrode 3a changes with the air-fuel ratio. FIG. 3C shows that the terminal voltage of electrode 3a can vary between $V_1$ and $V_2$, for example, for a time period $t_i$ when the voltage is being applied to the electrolyte. The electromotive force E, on the other hand, remains constant when measured during subsequent time interval $t_e$ whether the terminal voltage of electrode 3a has been at the $V_1$ level or $V_2$ level. FIG. 3C shows the terminal voltage 3a remaining constant during the time period $t_i$ and for each of the three successive periods shown, but the terminal voltage can change during a time interval $t_i$ changes from one time period to another as the air-fuel ratio being sensed or temperature of the sensor changes. Therefore, in the case of a changing air-fuel ratio, the applied voltage of FIG. 3A changes to maintain the electromotive force E constant, but the air-fuel ratio is shown in FIG. 3C as remaining constant.

Figure 4A:
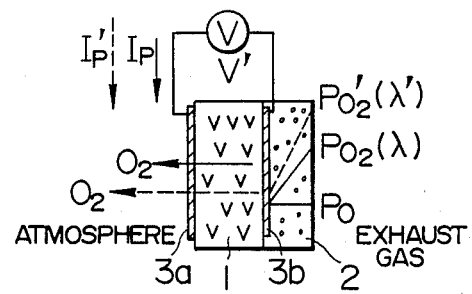

Now, explanation will be made of the relationship between the change in the oxygen concentration distribution in the diffusion resistor 2 with the air-fuel ratio and the movement of oxygen or current $I_P$, with reference to FIG. 4. FIG. 4A shows the operation in the lean region, in which the current $I_P$, the movement of oxygen and oxygen concentration distribution for the air-fuel ratio less than a predetermined value $\lambda$ are shown in solid lines, and those for the air-fuel ratio taking another value $\lambda'$ by dotted lines. In this drawing, the relations $\lambda' > \lambda > 1$ are assumed to hold. When the air-fuel ratio is $\lambda$, the oxygen concentration of the exhaust gas is $P_{O2}$, and the oxygen concentration on exhaust gas side of the diffusion resistor 2 also takes the value $P_{O2}$. The current $I_P$ is applied in such a manner that the electromotive force E takes a predetermined value on the basis of the electromotive force E measured during a previous timing, and therefore the oxygen in the diffusion resistor 2 is drawn out into the atmosphere with the result that the oxygen concentration in the vicinity of the electrode 3b remains at the predetermined value $P_O$. If the electromotive force E is 0.5 V, for instance, the value $P_O$ is approximately $10^{-12}\%$. When the air-fuel ratio changes to $\lambda'$ ($\lambda' > \lambda$), the oxygen concentration on the exhaust side of the diffusion resistor 2 increases to $P_{O2}'$. Since the current $I_P'$ larger than $I_P$ is applied to keep the electromotive force E constant, the oxygen concentration in the vicinity of the electrode 3b is kept at a predetermined value $P_O$. In this way, in the case where the oxygen concentration changes from $P_{O2}$ into $P_{O2}'$ ($P_{O2} < P_{O2}'$), it is necessary to move a great amount of oxygen in order to keep $P_O$ constant. Specifically, the voltage V is changed into V' (V' > V) thereby to increase $I_P$ to $I_P'$ ($I_P' > I_P$). As a result, the current value, that is, the voltage value involved is proportional to the air-fuel ratio.

Figure 4B:
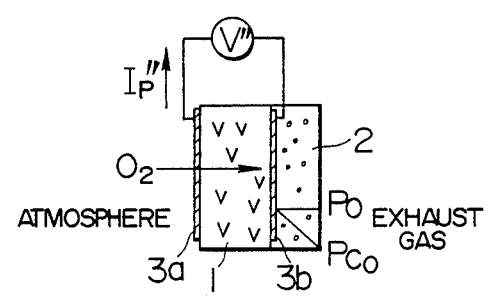

FIG. 4B shows the operation in the rich-mixture region. In this rich-mixture region where the air-fuel ratio is $\lambda''$ ($\lambda'' < 1$), such combustible gas as CO is generated, and therefore, if the oxygen concentration in the vicinity of the electrode 3b is to be $P_O$, it is necessary to supply oxygen gas from the atmosphere into the exhaust side. For this purpose, the polarity of the voltage applied to the solid electrolyte 1 is reversed and the current $I_P''$ is applied in the direction opposite to that for the lean-mixture region. This operation keeps the oxygen concentration in the vicinity of the electrode 3b at $P_O$. The solid line in the diffusion resistor 2 represents the concentration distribution of carbon monoxide CO which is $P_{CO}$ on exhaust side, $P_O$ being substantially zero on the electrode 3b side. When the air-fuel ratio further decreases from $\lambda''$, a great amount of CO comes to exist and diffuses into the diffusion resistor 2, and therefore, if the oxygen concentration near the electrode 3b is to be kept at $P_O$, an increased amount of oxygen is required to be supplied. For this purpose, the voltage V'' is increased to increase the current $I_P''$. In other words, the voltage V'' changes with the air-fuel ratio.

On this principle, it is possible to measure the air-fuel ratio from rich-mixture to lean-mixture regions. It is, however, necessary to reverse the direction of current. This operation is automatically performed without detecting the point of $\lambda = 1.0$ in the embodiment described below. Now, such an embodiment will be explained below.

Figure 5A:
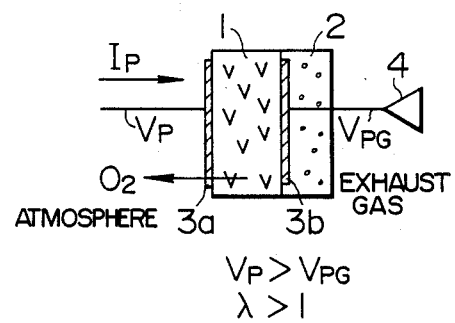
Figure 5B:
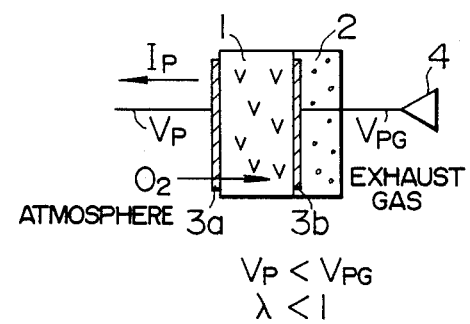

FIG. 5A shows a diagram for explaining the operation of the lean-mixture region. The electrode 3b on the exhaust side is connected to a potential ground 4 having a predetermined potential $V_{PG}$. For supplying the current $I_P$ in the direction of the arrow in the lean-mixture region, the voltage $V_P$ of the electrode 3a is rendered higher than $V_{PG}$. Specifically, oxygen is drawn out of the diffusion resistor 2 toward the atmosphere under the condition where $V_P$ is higher than $V_{PG}$. In the rich-mixture region shown in FIG. 5B, on the other hand, the voltage $V_P$ is rendered smaller than $V_{PG}$, so that the current $I_P$ flows in the direction opposite to that for the lean-mixture region, thus supplying oxygen into the diffusion resistor 2.

As explained above, by connecting the electrode 3b to the potential ground 4 and changing the voltage on electrode 3b side, the direction of current $I_P$ can be reversed automatically. The construction of this potential ground will be described later.

Figure 6:
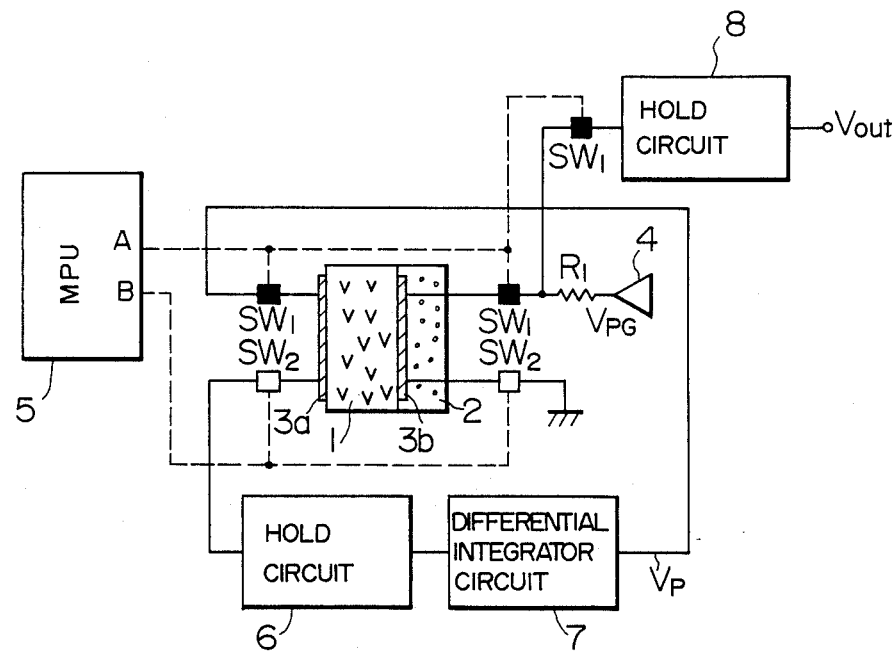
FIG. 6 is a schematic diagram showing an embodiment of the present invention.

A general configuration of the drive circuit for the detection system according to an embodiment of the present invention is shown in FIG. 6. Numeral 5 designates a microcomputer for applying on-off signals to the terminals A and B alternately. This microcomputer may be replaced with equal effect by an ordinary oscillator or an oscillation circuit including a capacitor and a resistor. When the ON signal is applied to the terminal A, the switch $SW_1$ is turned on (conducts), while an OFF signal is applied to the terminal B thereby to turn off (cuts off) the switch $SW_2$. When the switch $SW_1$ is turned on, the current $I_P$ flows in the solid electrolyte 1. During the following period, the on-off states of the terminals A and B are reversed so that the switch $SW_2$ is turned on while the switch $SW_1$ is turned off. During the period when the switch $SW_2$ is on, the electromotive force E is measured. The electromotive force E detected during this period is held by a hold circuit 6, and the electromotive force E is thus maintained at a predetermined value even when the switch $SW_2$ is turned off. At the next moment, a differential integration circuit 7 compares the electromotive force E with a reference value $E_{ref}$, and if the former is smaller than the latter, the output $V_P$ of the differential integration circuit 7 continues to increase. This voltage $V_P$ is applied to the solid electrolyte 1 when the switch $SW_1$ is turned on. In the case where the voltage E is higher than $E_{ref}$, by contrast, the output $V_P$ of the differential integrator 7 continues to decrease. In this way, the output $V_P$ undergoes a change to control the current $I_P$ in such a manner that the electromotive E approaches $E_{ref}$. In the rich-mixture region, by the way, the output $V_P$ is reduced to become smaller than $V_{PG}$ as mentioned above.

In order to obtain a circuit output, a fixed resistor $R_1$ is inserted between the potential ground 4 and the electrode 3b, and the terminal voltage is held by a hold circuit 8, thus producing an output $V_{out}$. The potential ground 4 is a constant voltage source always supplied with a constant voltage. Since the resistor $R_1$ is fixed in value, the output $V_{out}$ takes a value proportional to the current $I_P$.

Figure 7:
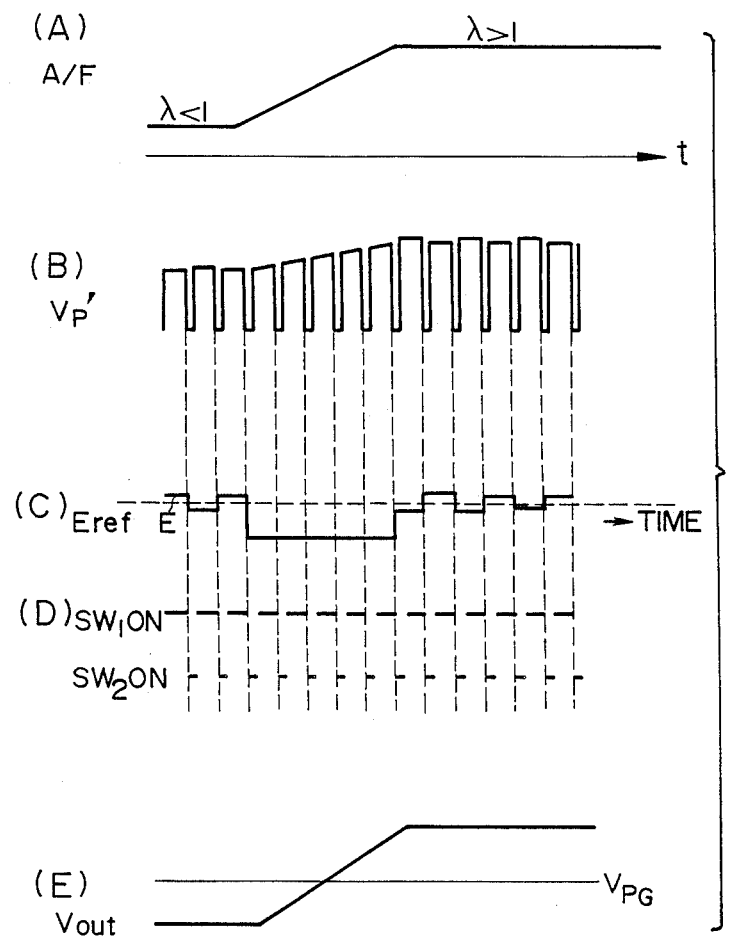
FIGS. 7 to 12 are diagrams for explaining the operation and characteristics of an embodiment of the present invention.

FIG. 7 shows a diagram for explaining the signal levels of various parts and the operation of the switches $SW_1$ and $SW_2$ with the air-fuel ratio changing from rich-mixture to lean-mixture regions. FIG. 7A shows an actual change in air-fuel ratio from a point smaller than 1 to a point larger than 1. FIG. 7B shows $V_P'$ applied to the electrode 3a through the switch $SW_1$, and FIG. 7C the electromotive force E applied to the differential integration circuit 7. If the air-fuel ratio undergoes an abrupt change into the lean-mixture region, the amount of oxygen in the diffusion resistor 2 increases, and therefore the electromotive force E decreases below the voltage $E_{ref}$. As a result, the output $V_P$ of the differential integration circuit 17 continues to increase. When the air-fuel ratio settles at a certain value soon, the output $V_P$ also converges to a predetermined value. In the process, the electromotive force E converges to $E_{ref}$. FIGS. 7C and 7D show the periods during which the switches $SW_1$ and $SW_2$ are turned on respectively. The on-off period of these switches should be sufficiently short as compared with the normal time of air-fuel ratio change. FIG. 7G shows the voltage $V_{out}$, which is smaller than $V_{PG}$ in the rich-mixture region and becomes higher than $V_{PG}$ in the lean-mixture region.

As explained above, this circuit changes the output $V_P$ in such a manner that the electromotive force E is rendered $E_{ref}$. In the case where the air-fuel ratio changes from the lean-mixture into rich-mixture region, on the other hand, the output $V_P$ decreases, and so does the output $V_{out}$.

Figure 8:
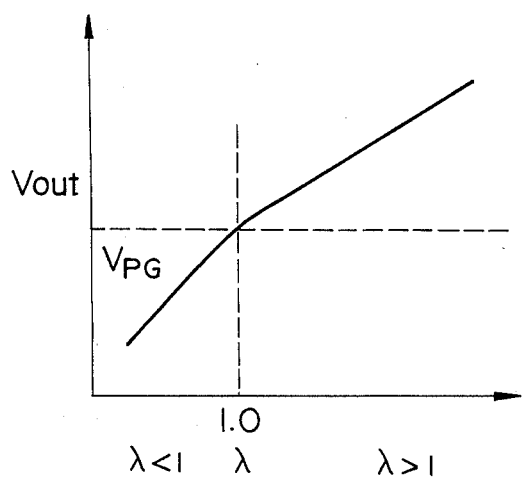

FIG. 8 shows relationship between the air-fuel ratio (air excess rate) $\lambda$ and the voltage $V_{out}$. When $\lambda$ is 1.0, the current $I_P$ is theoretically zero, and therefore $V_{out}$ is $V_{PG}$. When $\lambda$ is smaller than one, $V_{out}$ is smaller than $V_{PG}$, while when $\lambda$ is larger than 1, the voltage $V_{out}$ is larger than $V_{PG}$. Specifically, the direction of the current $I_P$ reverses automatically at the $\lambda$ values of 1.0, thus making it possible to continuously measure the air-fuel ratio from the rich-mixture to lean-mixture regions.

Figure 9:
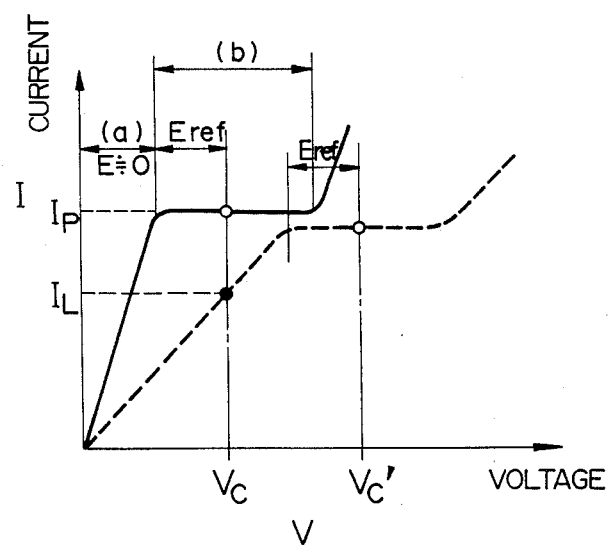

The physical meaning of the operation of the detection system according to the present invention will be explained. FIG. 9 is a characteristic diagram showing the current value I which changes with the increase in the voltage V applied to the solid electrolyte. When the voltage V is increased from zero, the current I increases in proportion to the voltage V by the conduction of oxygen ions in the range (a). With further increase in voltage V, the flow of oxygen is controlled by the function of the diffusion resistor 2, and the current I does not easily change with the increase in the voltage V (range (b)). Under this condition, the current I takes a value called the critical value.

The operating principle of the circuit shown in FIG. 6 with the air-fuel ratio fixed at a predetermined value will be explained with reference to the characteristic represented by a solid line in FIG. 9. Assume that the output $V_P$ of the differential integration circuit 7 is included in the range (a). The electromotive force E generated between the terminals is substantially zero. As a result, the differential integration circuit 7 increases the output $V_P$. Soon later, when the output V begins to enter the range (b), an electromotive force also begins to be generated across the terminals, and when the electromotive force becomes $E_{ref}$, the output $V_P$ stops increasing and converges to $V_C$. Under this condition, the current $I_P$ flows in the solid electrolyte 1. This current $I_P$ is equal to the above-mentioned critical current value and takes a value proportional to the air-fuel ratio.

The characteristic illustrated by dotted lines in FIG. 9, on the other hand, is associated with low temperatures of the solid electrolyte 1. If the output $V_P$ remains at $V_C$, the current value is $I_L$ which is not a critical current. In the circuit of the present invention, however, E is decided to be almost zero when $V_P$ is equal to $V_C$, and therefore the output $V_P$ continues to increase further until it converges to $V_C'$ where the electromotive force E is $E_{ref}$. As a result, the current flowing in the solid electrolyte under this condition also takes a critical current value. In this way, in the detection system according to the present invention, a current equivalent to the critical current value is always applied to the solid electrolyte 1 against the variations in the temperature of the solid electrolyte 1.

Figure 10:
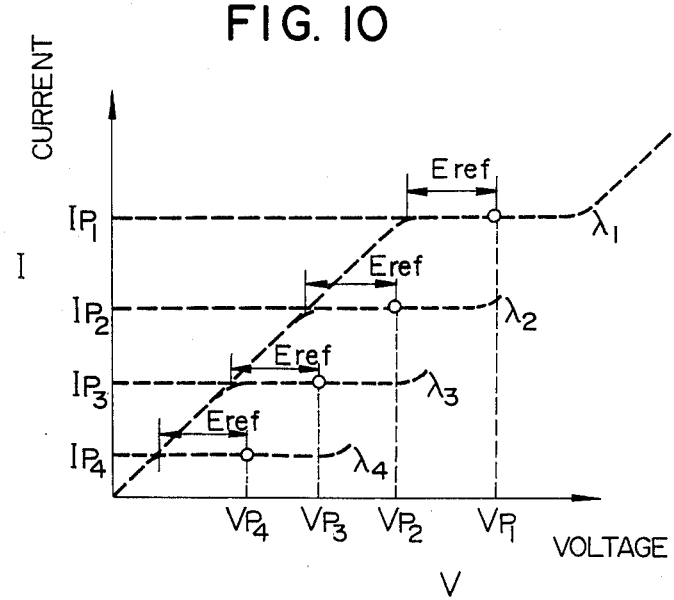

FIG. 10 is a characteristic diagram for different values $\lambda_1$, $\lambda_2$, $\lambda_3$ and $\lambda_4$ ($\lambda_1 > \lambda_2 > \lambda_3 > \lambda_4$) of the air-fuel ratio $\lambda$ with the temperature of the solid electrolyte 1 kept constant. When the air-fuel ratio is $\lambda_1$, it is necessary to apply the voltage $V_{Pl}$ to the solid electrolyte 1 if the electromotive force across the terminals is to be $E_{ref}$, and therefore the output $V_P$ increases to $V_{P1}$ and converges to $V_{P1}$. Under this condition, the current $I_{P1}$ flows, which coincides with the critical current value for the air-fuel ratio $\lambda_1$. If the air-fuel ratio changes to $\lambda_2$, on the other hand, the output $V_{PH}$ decreases and converges to $V_{P2}$, and the current takes a value of $I_{P2}$. In similar fashion, when the air-fuel ratio is $\lambda_3$ and $\lambda_4$ the critical currents $I_{P3}$ and $I_{P4}$ flow in the solid electrolyte 1 respectively. The circuit shown in FIG. 6 produces an output proportional to such a current, and therefore is always capable of monitoring the critical current value.

Figure 11:
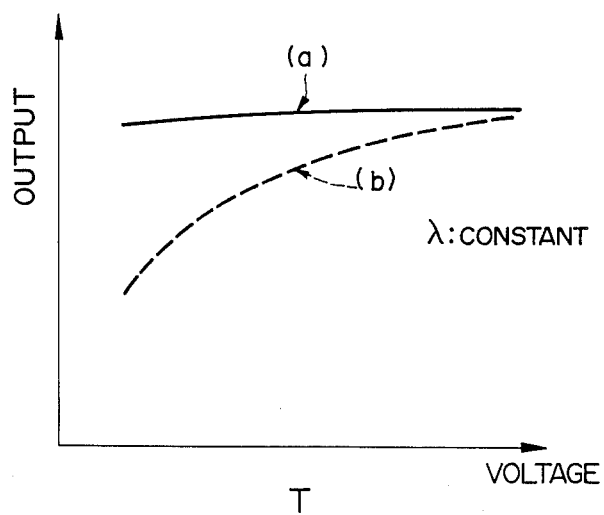

FIG. 11 shows variations in output with temperature T of the solid electrolyte 1. In this case, the air-fuel ratio is kept constant. Curve (b) shows a characteristic with a constant voltage $V_C$ applied to the solid electrolyte 1 as seen from FIG. 9, and curve (a) an output characteristic of the detection system according to the present invention. As described above, the temperature dependency of the output is small since the critical current value can be monitored against changes in temperature T.

Figure 12:
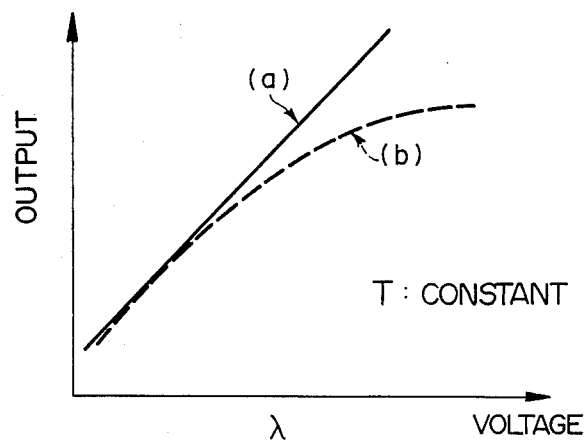

FIG. 12 shows an output characteristic with the air-fuel ratio $\lambda$ changed at a constant temperature T. A characteristic with a constant voltage applied to the solid electrolyte 1 is shown in curve (b). As will be seen from FIG. 10, if the voltage is fixed at $V_{P3}$, for instance, it becomes impossible to measure the critical current with the increase in air-fuel ratio $\lambda$, with the result that as shown in curve (b), the gain for the air-fuel ratio $\lambda$ is reduced for a large value of the latter. The characteristic shown in curve (a) is that of the detection system according to the present invention, indicating that even when the air-fuel ratio λ changes, the voltage $V_P$ is changed to measure the critical current value, so that the gain of the output value against the air-fuel ratio λ remains the same with the increase in λ.

Figure 13:
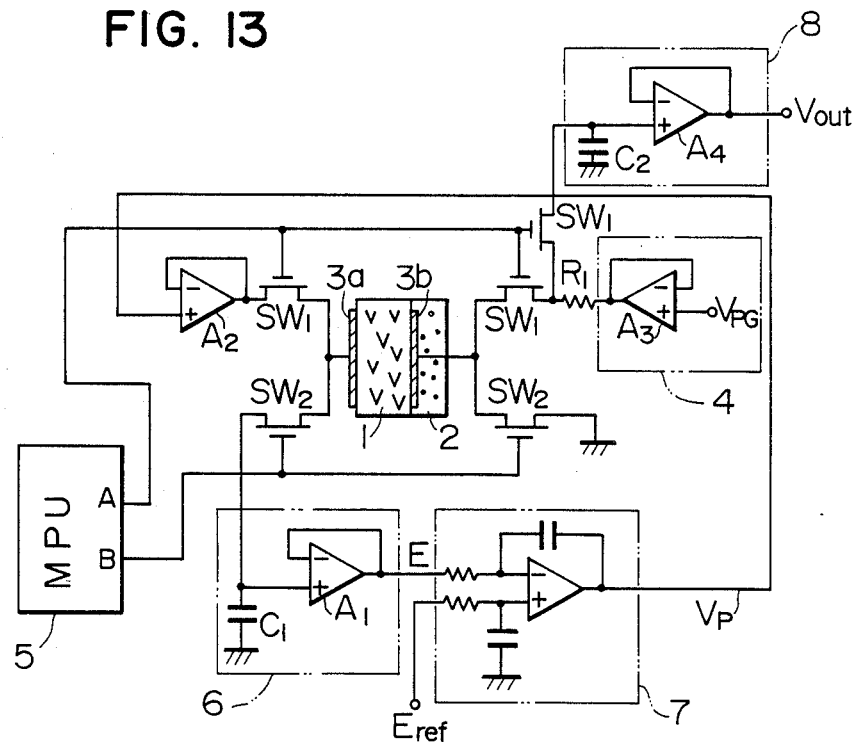
FIG. 13 shows the construction of an embodiment of the present invention.

FIG. 13 shows an example of a specific circuit configuration of the detection system according to the present invention. Numeral 5 designates a microcomputer or an oscillator for producing a switching signal. A hold circuit 6 includes a capacitor $C_1$ and a buffer amplifier $A_1$. The electromotive force E held at the hold circuit 6 is applied to a differential integration circuit 7. This differential integration circuit 7 compares the electromotive force E with the reference voltage $E_{ref}$. If E is smaller than $E_{ref}$, the voltage $V_P$ continues to increase, while if E is larger than $E_{ref}$, the voltage $V_P$ continues to decrease. This integrating operation is continued until the electromotive force E converges to $E_{ref}$, and after E thus converges, the voltage $V_P$ also settles to a predetermined value. This voltage $V_P$ is applied through a buffer amplifier $A_2$ and a switch $SW_1$ to the electrode 3a. The potential ground 4, on the other hand, includes a buffer amplifier $A_3$ and produces a constant voltage $V_{PG}$. Assume that the switch $SW_1$ is turned on, and the voltage $V_P$ is applied to the solid electrolyte 1. If $V_P$ is higher than $V_{PG}$, the current flows through the buffer amplifier $A_2$ and the solid electrolyte 1 and drops to the ground in the buffer amplifier $A_3$. The potential ground, however, is kept constant at $V_{PG}$. In the case where $V_P$ is smaller than $V_{PG}$, on the other hand, the current flows through the buffer amplifier $A_3$ and the solid electrolyte 1 and drops to the ground level in the buffer amplifier $A_2$, although the output of the buffer amplifier $A_2$ is kept constant at $V_P$. The terminal voltage ($V_{out}$) of the resistor $R_1$ with the switch $SW_1$ turned on is held and produced by the buffer amplifier $A_4$ and the capacitor $C_2$ of the output circuit 8. This circuit permits detection of the air-fuel ratio according to the present invention.

Figure 14:
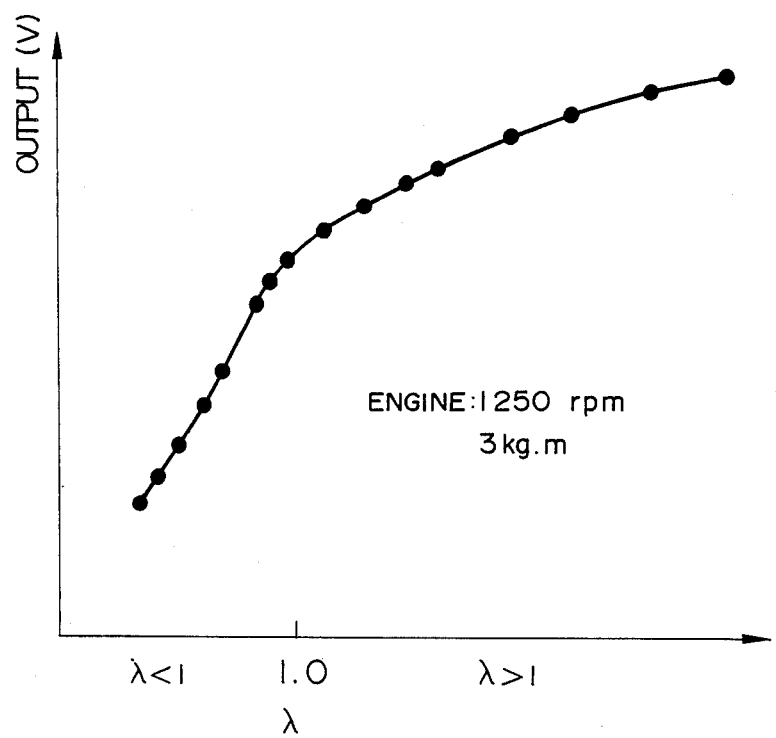
FIG. 14 is a diagram showing the results of an experiment conducted on the same.

FIG. 14 shows the result of measuring the actual engine exhaust gas according to an embodiment of the present invention mentioned above. The sensor of the detection system is mounted on the exhaust manifold of the engine which is driven at the speed of 1250 rpm and torque of 3 kg.m constant. In FIG. 14, the abscissa represents the air-fuel ratio λ, and the ordinate the output. As seen from FIG. 14, the air-fuel ratio can be measured over a wide range from a value smaller than 1 to larger than 1. The gain of the output value changes at the air-fuel ratio of 1. This is in view of the fact that when λ is larger than 1, the critical current $I_P$ depends on the oxygen concentration of the exhaust gas, while in the range of λ smaller than 1, the current $I_P$ is dependent on the combustible gases CO, HC and $H_2$ in the exhaust gas. Especially, because of the very high diffusion rate of $H_2$ in the combustible gas (about 4 times that of CO and $O_2$), a great amount of current is required, resulting in a large output.

Figure 15A:
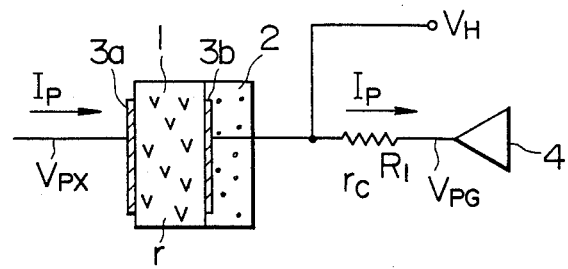
FIGS. 15A–15B to 17 are diagrams for explaining another embodiment of the present invention.

Now, explanation will be made of a temperature control method by which the internal resistance r is kept constant in order to keep the temperature of the solid electrolyte 1 constant. FIG. 15A shows the operation for the air-fuel ratio λ larger than 1. In this case, the current $I_P$ flows along the direction of the arrow in the drawing, and the relationship $V_P > V_H > V_{PG}$ holds where $V_P$ is the voltage on the electrode 3a, $V_H$ the voltage on the electrode 3b side, and the voltage on the potential ground 4 side of the resistor $R_1$. The values $V_P$, $V_H$ and $V_{PG}$ are correlated with each other as shown below.

$$V_P - V_H = E + rI_P \quad (1)$$

$$V_H - V_{PG} = r_c \cdot I_P \quad (2)$$

Where E is the electromotive force, $r_c$ the resistance value of the resistor $R_1$. From equation (1) above, the internal resistance r is given as $$r = \frac{V_P - V_H - E}{I_P} \quad (3)$$

In this equation, $V_H$ is known as it is always measured as an output, and E is also known as it is controlled always to a predetermined value. Assuming that $$V^* = V_H + E \quad (4)$$

equation (3) is rewritten as $$r = \frac{V_P - V^*}{I_P} \quad (5)$$

Or from equation (2), $I_P$ is expressed as $$I_P = \frac{V_H - V_{PG}}{r_c} \quad (6)$$

Since the values $V_H$, $V_{PG}$ and $r_c$ are known, $I_P$ is also known. As a result, the internal resistance r of the solid electrolyte 1 can be calculated from equations (5) and (6).

Figure 15B:
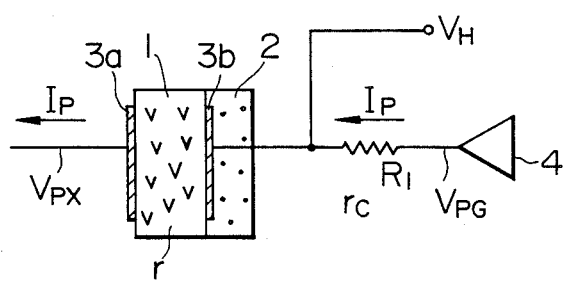

The operation in the case of λ smaller than 1 is shown in FIG. 15B. In this case, the current $I_P$ flows in the direction opposite to that for FIG. 15A, and therefore the voltages at the respective parts hold the relationship $V_P < V_H < V_{PG}$. After the calculations of equations (1) to (6), the relationship between $V_P$, $V_H$ and $V_{PG}$ is given as $$V_P - V_H = E - rI_P \quad (7)$$

$$V_{PG} - V = r_c \cdot I_P \quad (8)$$

Equation (7) is rewritten from equation (4), as $$r = \frac{V^* - V_P}{I_P} \quad (9)$$

From equation (8), on the other hand, $I_P$ is expressed as $$I_P = \frac{V_{PG} - V_H}{r_c} \quad (10)$$

Figure 16:
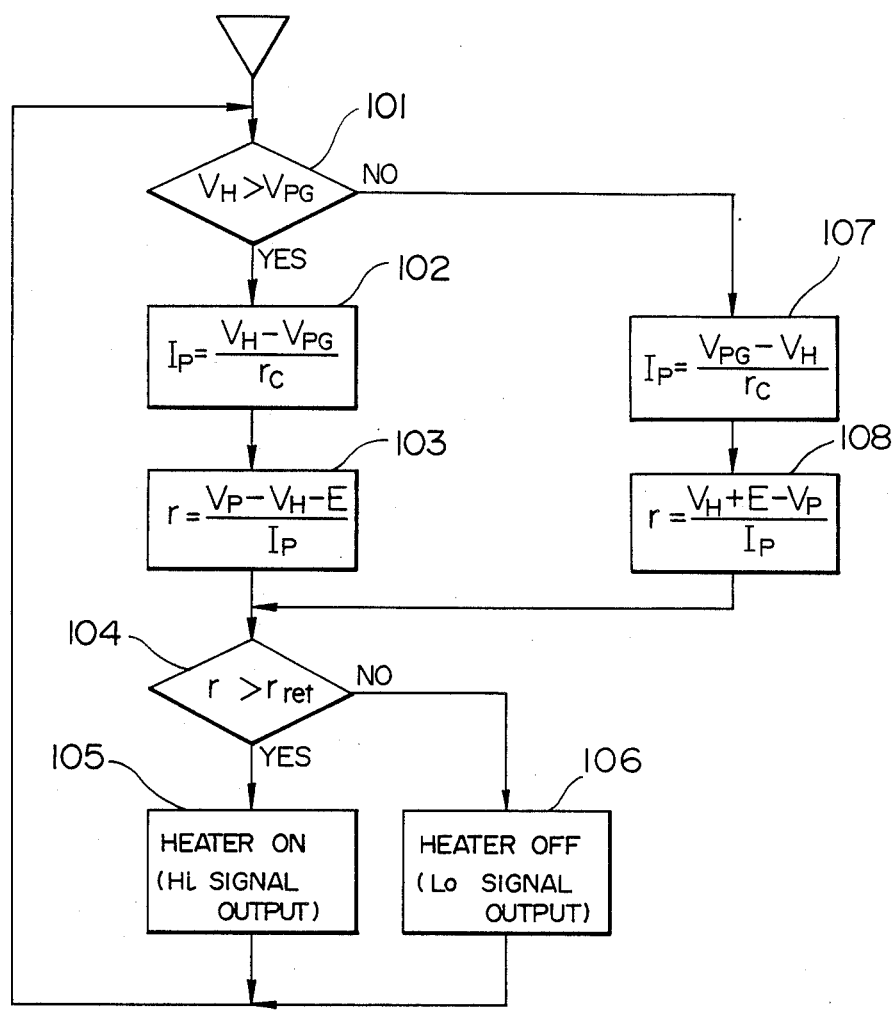

Since $V_{PG}$, $V_H$, $r_c$ and $V^*$ are known, the internal resistance r is obtained from equations (9) and (10). By calculating this internal resistance r, the heater is controlled thereby to keep the internal resistance r constant. FIG. 16 shows the flow of heater control. This calculation is different between the values of λ larger and smaller than 1. First, this decision is made by the fact that the relative magnitudes of $V_H$ and $V_{PG}$ change depending on the direction of the current $I_P$ (step 101).

When λ is larger than 1, $V_H$ is larger than $V_{PG}$, and therefore the current $I_P$ is calculated from equation (6) (step 102). Then, the internal resistance r is calculated from this current $I_P$ and equation (5) (step 103). This internal resistance r is compared with the resistance value $r_{ref}$ to be controlled (step 104). If r is larger than $r_{ref}$, the temperature of the solid electrolyte 1 is lower than a set value, and therefore a signal Hi for turning on the heater is produced thereby to heat the solid electrolyte 1 (step 105). If r is smaller than $r_{ref}$, by contrast, T is higher than a set value, and therefore a signal Lo for turning off is generated (step 106). After that, the process is returned to step 101.

In the case where $V_H$ is smaller than $V_{PG}$, on the other hand, λ is smaller than 1.0, and therefore the current $I_P$ is calculated from equation (10) (step 107). From this $I_P$ and equation (9), the internal resistance is calculated (step 108). After the internal resistance is obtained this way, the process proceeds to step 104, followed by the same flow of steps as before for controlling the heater. Although this flow of operation can be processed by an analog circuit, it is more advantageous to use a digital circuit with A/D conversion connected to the microcomputer 5.

Figure 17:
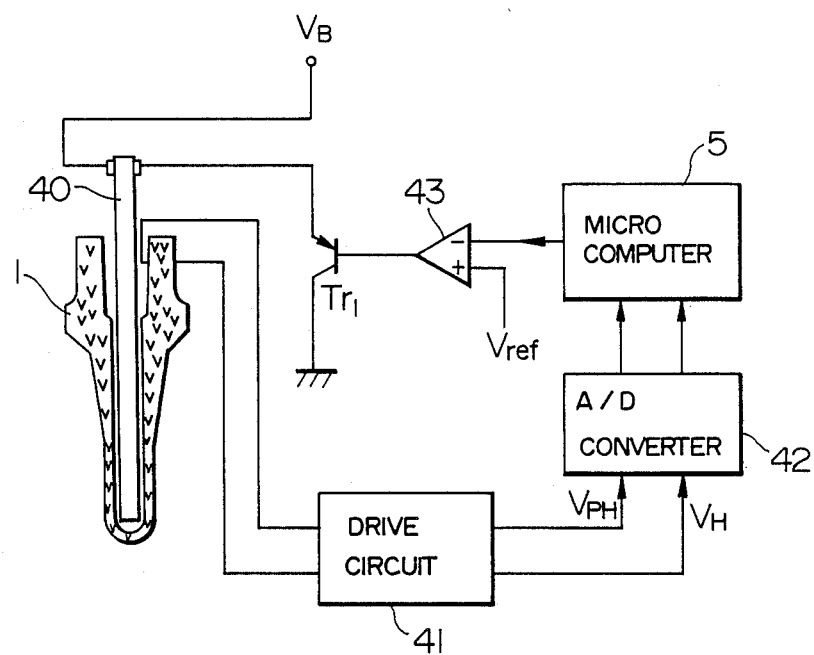

FIG. 17 is a wiring diagram for a circuit for controlling the heater. The above-mentioned outputs $V_{PH}$ and $V_H$ are applied to an A/D converter 42 from a drive circuit 41 of the detection system. Digital values corresponding to $V_{PH}$ and $V_H$ are applied to the microcomputer 5. In the microcomputer 5, the flow of operations shown in FIG. 16 is executed, and signals Hi and Lo are applied to the comparator 43. If a signal Hi is produced, the comparator 43 applies a signal Lo to the base of the transistor $T_{r1}$, so that the transistor $T_{r1}$ begins to conduct, and current flows in the heater 40, thus heating the solid electrolyte 1.

When a signal Lo is produced from the microcomputer 5, by contrast, the comparator 43 produces a signal Hi, with the result that the transistor $T_{r1}$ is cut off, so that no current flows in the heater 40. In this manner, the heater control is executed by hardware, thus keeping the temperature of the solid electrolyte 1 always constant.

Figure 18A:
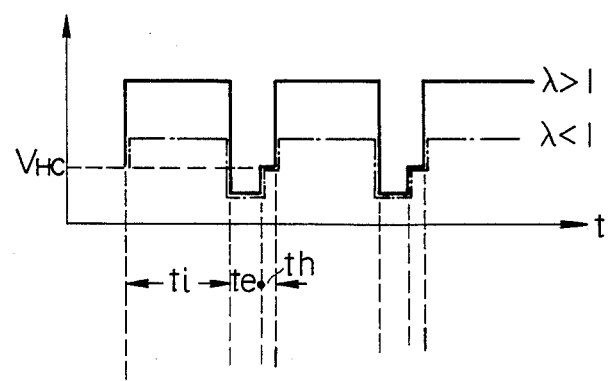
FIGS. 18A–18C and 19 are diagrams for explaining still another embodiment of the present invention.
Figure 18B:
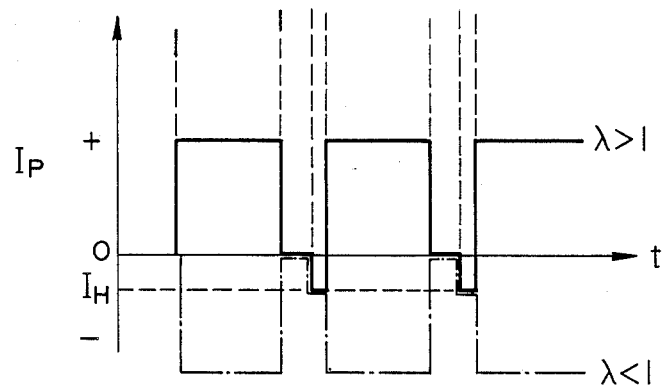
Figure 18C:
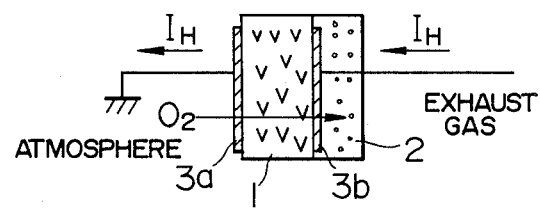

Another method of controlling the heater is shown in FIG. 18. This method is such that as shown in FIG. 18A, a period $t_h$ for measuring the internal resistance r of the solid electrolyte 1 by supplying a predetermined value of current is newly provided in addition to the period $t_i$ for supplying the current $I_P$ and the period $t_e$ for measuring the electromotive force E. As shown in FIG. 18B, the constant current $I_H$ is supplied during the period $t_h$, and by detecting the terminal voltage $V_{HC}$ involved, the internal resistance r is measured. In the process, as shown in FIG. 18C, the current $I_H$ is supplied in such a direction as to supply oxygen into the diffusion resistor 2. The terminal voltage $V_{HC}$ is thus expressed as $$V_{HC} = rI_H - E \tag{11}$$

$$V_{HC} \propto r \tag{12}$$

As seen from equation (12), the voltage $V_{HC}$ is a function of the internal resistance r since the values $I_H$ and E are known. Specifically, if the heater is controlled in such a manner as to keep the voltage $V_{HC}$ by measurement, an accurate temperature control is possible. The solid lines in FIGS. 18A and 18B represent the case where λ is larger than 1, and the one-dot chains the case where λ is smaller than 1. As shown in FIG. 18B, if λ is smaller than 1, the direction of the current $I_P$ is opposite to the case where λ is larger than 1, and therefore is indicated with minus sign.

During the period $t_h$ when the current $I_H$ is supplied in the direction of FIG. 18C, oxygen is supplied to the exhaust side, indicative of the fact that the solid electrolyte 1 is protected in the rich-mixture region.

Figure 19:
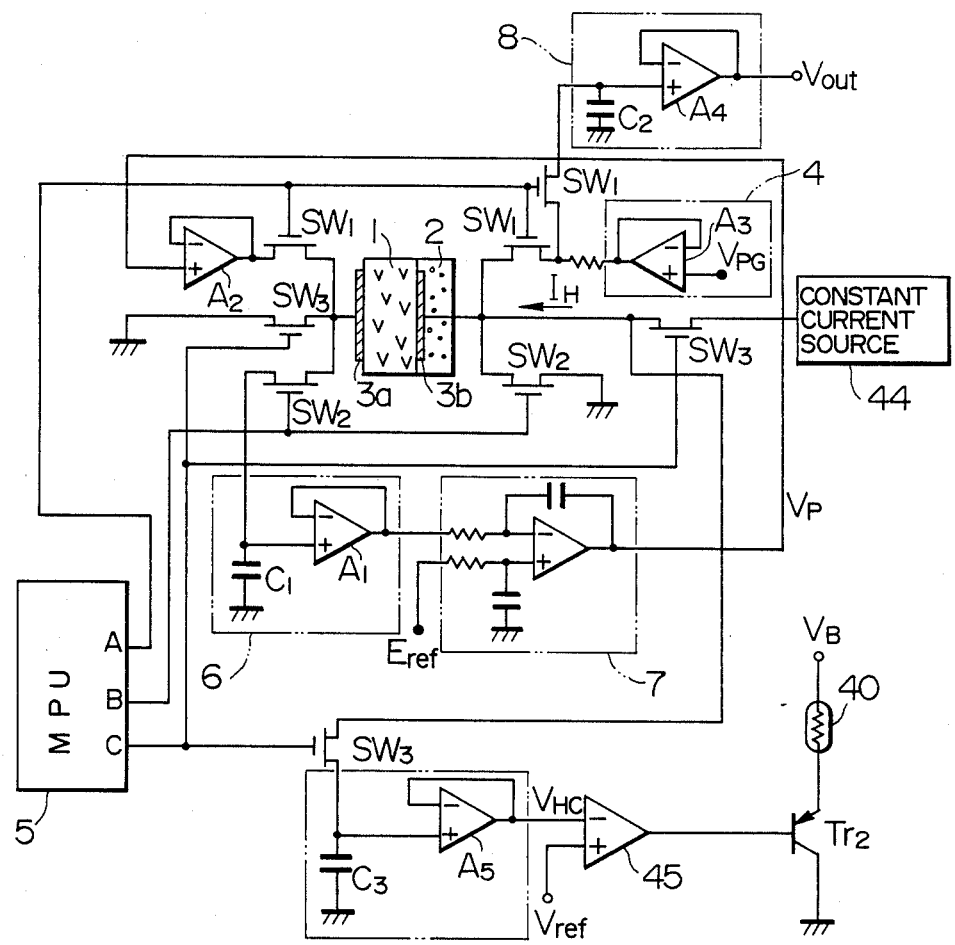

FIG. 19 shows a circuit configuration for realizing the operation illustrated in FIG. 18. A signal for turning on during the period $t_i$ is produced from the terminal A of the microcomputer 5, a signal for tuning on during the period $t_e$ from the terminal B, and a signal for turning on during the period $t_h$ from the terminal C. As a result, only the switch $SW_3$ is turned on during the period $t_h$. Upon conduction of this switch $SW_3$, a constant current $I_H$ flows from a constant current source 44 to the solid electrolyte 1. The terminal voltage $V_{HC}$ generated under this condition is sample-held by a capacitor. $C_3$ and a buffer amplifier $A_5$. Even in the case where the switch $SW_3$ is not conducting, therefore, the output of the buffer amplifier $A_5$ is held at $V_{HC}$. This output $V_{HC}$ is compared with the reference voltage $V_{ref}$, and if $V_{HC}$ is larger than $V_{ref}$, an off signal is applied from the comparator 45 to the base of the transistor $T_{r2}$. As a result, the transistor $T_{r2}$ begins to conduct, so that current is supplied to the heater 40 thereby to heat the solid electrolyte 1. If $V_{HC}$ is smaller than $V_{ref}$, in contrast, an on signal is produced from the comparator 45, and therefore the transistor $T_{r2}$ is cut off with the result that current ceases to flow in the heater 40. A value of $V_{ref}$ corresponding to the internal resistance r desired is determined in advance by equation (11). In this manner, while monitoring the internal resistance 5 of the solid electrolyte 1, a highly accurate temperature control becomes possible.

The general configuration of another embodiment of the present invention will be explained with reference to FIG. 20. The potential ground circuit 84 including a voltage source 64 for the potential $V_{PG}$ and a buffer amplifier 65 holds the output voltage of the amplifier 65 at a predetermined value higher by $V_{PG}$ than the circuit ground. As a consequence, the potential of the electrode 53 in contact with the exhaust gas environment through the diffusion resistor 54 of porous material is always higher than the circuit ground, so that it is possible to measure the positive and negative pump currents $I_P$ moving in the zirconia solid electrolyte 50. The resistor 66 is for detecting the pump current $I_P$, and by converting the current $I_P$ into an output voltage $e_0$, applied to the microcomputer for engine control from the circuit 88 including the buffer amplifier 67 and the capacitor 62.

Assume that a pulse train A of a time-sharing signal generator 85 is off, and a pulse train B on. The switches 68 and 69 including CMOS are turned off. With the turning off of the switch 69, there is no exciting voltage supplied from the integrator circuit 87 to the electrode 52, thereby forcibly reducing to zero the pump current $I_P$ flowing in the zirconia solid electrolyte 50. Under this condition, the potential difference between the electrodes is limited to the component of the electromotive force eλ, and therefore this component is detected by a differential amplifier circuit 89 including resistors 71 to 74 and an amplifier 75. It is thus possible to detect the electromotive force eλ with high accuracy without being affected by Ohm loss voltage. Since the switch 76 is on, the value $e\lambda$ detected by the differential amplifier circuit 89 is transferred quickly to a hold circuit 86 including a capacitor 77 and an amplifier 78. This value $e\lambda$ is applied to an integrator circuit 87, and is compared with the reference voltage $E_{ref}$. The time constant $\tau$ of the integrator circuit 87 is determined from the values of the resistor 79 and the capacitor 80, and is set to a value of several to several tens of ms. The reference voltage $E_{ref}$, on the other hand, is set to a value of 0.3 to 0.6 volts. When $e\lambda$ is smaller than $E_{ref}$, the circuit functions to increase the excitation voltage applied to the electrode 52, while when $e\lambda$ is larger than $E_{ref}$, the circuit works to decrease the excitation voltage.

When the pulse trains A and B of the timesharing signal generator 85 are reversed, the switch 69 is turned on, and the excitation voltage is applied from the integrator circuit 87 to the electrode 52. If $e\lambda$ is smaller than $E_{ref}$, the excitation voltage is high, so that the circuit functions to draw out much oxygen from the electrode 53 in rich-mixture state while reducing the amount of oxygen supplied to the electrode 53 in rich-mixture state, with the excitation voltage being subjected to feedback control to render $e\lambda$ equal to $E_{ref}$.

When $e\lambda$ is larger than $E_{ref}$, by contrast, the excitation voltage becomes small, and therefore a smaller amount of oxygen is drawn out from the electrode 53 in lean-mixture state, while a larger amount of oxygen is supplied to the electrode 53 in rich-mixture state. In similar fashion, the excitation voltage is controlled by feedback so that $e\lambda$ may be equal to $E_{ref}$. The feedback control is effected into an equilibrium state by the electrochemical oxygen pump action. In order that the excitation voltage may not be sampled, the switch 76 is turned off, while the switch 68 is turned on, with the result that a voltage corresponding to the pump current $I_P$ detected by the detection resistor 66 is sampled, and is produced as an output voltage $V_{out}$ from the output circuit 88 including the capacitor 62 and the buffer amplifier 67.

By these alternate repetitive actions, the air-fuel ratio in the rich-mixture region, stoichiometric region and the lean-mixture region are capable of being detected continuously.

It is necessary that the time for detecting the electromotive force be kept not more than several ms in view of the fact that the electromotive force $e\lambda$ undergoes a slow change by the gas diffusion in the diffusion resistor 54.

In the case where the diffusion resistor 54 is produced with the switch 69 of CMOS to increase the critical current value $I_P$, for instance, the voltage drop through the internal resistance thereof is considerable, and therefore a switch like a transistor is desirable. In such a case, current is required to be supplied in two directions (positive and negative) with a pair of transistors to make bidirectional movement of current possible.

The integrator circuit 87 may be comprised of a differential amplifier with an appropriate gain.

Figure 20:
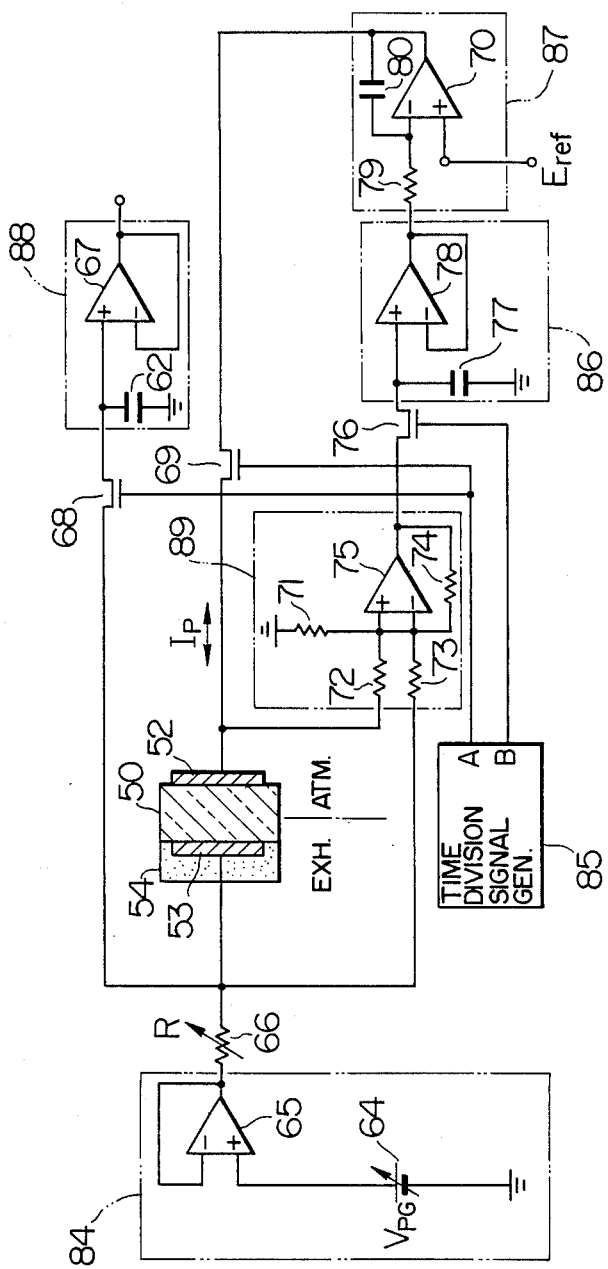
FIGS. 20 and 21 are diagrams for explaining a further embodiment of the present invention.

Anyway, the air excess rate $\lambda$ is capable of being detected with high accuracy by the configuration shown in FIG. 20 even when the excitation voltage between the electrodes becomes several times higher than the electromotive force $e\lambda$.

As a result, even in the case where the temperature of the zirconia solid electrolyte 50 is low (600° C. or higher according experiments), the heater power is reduced thereby to lengthen the service life thereof in operation.

Figure 21:
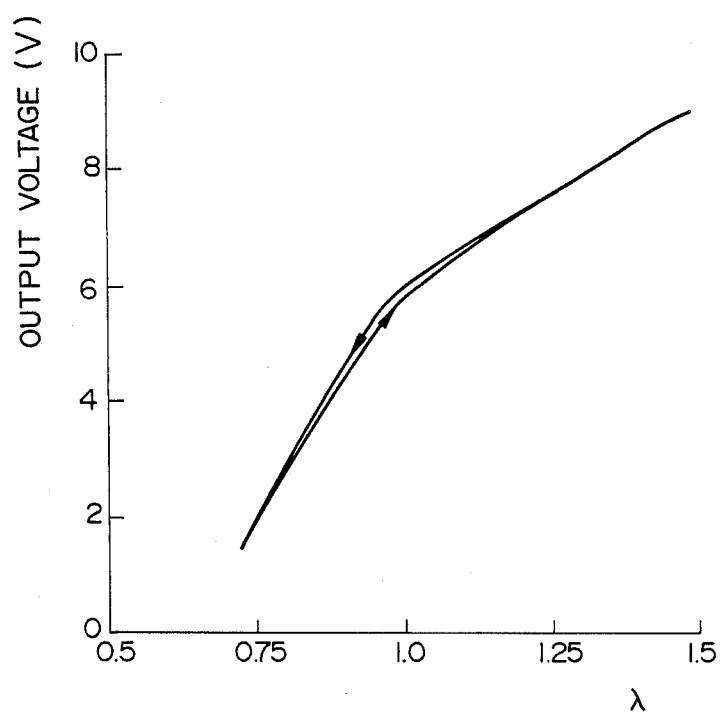

According to our experiments, in the event the sensor is exposed continuously to an environment of rich mixture for as long as several tens of minutes to several hours, the output characteristic develops a hysteresis probably due to local electron conduction of the zirconia solid electrolyte 50 in the vicinity of the electrode 53. An example of the result of this evaluation is shown in FIG. 21. By using a synthetic gas, the air excess rate $\lambda$ was reduced at uniform rate from 1.5 until it became 0.73 after about ten minutes. After the sensor was left to stand for about 70 minutes in a rich-mixture environment of 0.73 in $\lambda$, this value $\lambda$ was increased at uniform rate until it increased to 1.5 in about ten minutes. The resultant hysteresis is shown in the drawing. As seen from the drawing, the output voltage characteristic developed a hysteresis. The hysteresis was found to be larger the longer the sensor is left to stand in a rich-mixture environment or the smaller the value $\lambda$ of the environment in which it is left to stand.

An actual engine may be exposed for long time to a rich-mixture environment depending on the operating conditions, and therefore this hysteresis is of course not desirable for the purpose of control.

This experimental fact basically indicates that the time during which the excitation voltage is applied to the zirconia solid electrolyte 50 in a rich-mixture environment should be shortened. This remedial method was applied to the circuit configuration shown in FIG. 20.

Figure 22:
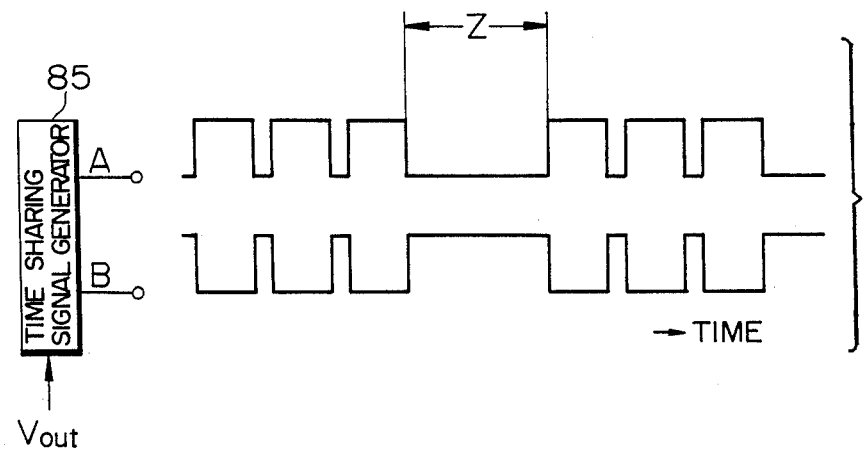
FIG. 22 is a diagram for explaining a still further embodiment of the present invention.

The same remedial method will be explained with reference to FIG. 22. In this method, a time-sharing signal generator 85 is controlled in accordance with the magnitude of the output voltage $V_{out}$ thereby to suspend the pulse trains A and B intermittently as shown in the section Z. As a result, the switch 69 in FIG. 20 is kept turned off for a comparatively long time (several tens to several hundreds ms) in accordance with the section Z, and during this time, the application of the excitation voltage to the zirconia solid electrolyte 50 is suspended. It is more effective if the length of the section Z is increased and the occurrence thereof is made more frequent with the decrease in $V_{out}$, that is, with the decrease in the value. Although this method sacrifices the measurement of air excess rate at each moment to some degree, this shortcoming may be compensated for by improving the control accuracy to a practically satisfactory extent by incorporating novel devices in the control algorithm.

Now, explanation will be made of application advantages obtained when the detection system according to the present invention is used for engine air-fuel ratio control.

In the case where the diffusion resistor 2 of this detection system changes in quality with time due to clogging or the like, the output thereof also undergoes a change. Since $I_P$ is zero when $\lambda$ is 1.0, however, the output $V_{out}$ takes the value equal to $V_{PG}$. In other words, since is the current $I_P$ is not supplied at this moment, the output remains at $V_{PG}$ regardless of the conditions of the diffusion resistor 2. More specifically, when $\lambda$ is 1, the oxygen concentration distribution in the diffusion resistor 2 is kept constant at $P_O$ ($P_O \neq 0$) even though the current $I_P$ is not supplied and therefore oxygen is not moved. This is by reason of the fact that the oxygen concentration in the exhaust gas is already $P_O$. As mentioned above, when $\lambda$ is 1.0, the voltage always remains constant at $V_{PG}$ in spite of the secular variation of the diffusion resistor 2 for lack of oxygen movement.

Even if the output changes with time, the output remains at $V_{PG}$ when λ is 1.0. This means that in the detection system according to the present invention, the air-fuel ratio λ of 1.0 can be measured with the same accuracy as a conventional oxygen sensor for detecting the stoichiometric air-fuel ratio. For this reason, when changing the engine air-fuel ratio according to the load, the amount of compensation for the injection amount of the fuel injection valve is determined at the time of controlling the value λ to 1.0.

In the process, the injection width $T_P$ is given as $$T_P = T_E(1+K_1+K_2+\ldots) \tag{13}$$

where $K_1$: Compensation factor by the air-fuel ratio detector, and $K_2$ and so on: Compensation factors by other than the air-fuel ratio detector (such as by detection of water temperature) The value $K_1$ is determined for the value λ of 1, and this value is utilized for controlling the air-fuel ratio to other levels.

In this way, compensation of the air-fuel ratio with high accuracy is made possible.

As explained above, according to each embodiment of the present invention, the advantages described below are obtained.

(1) The air-fuel ratio over a wide range from lean-mixture to rich-mixture range can be detected.

(2) The electromotive force Eλ is detected, and the excitation voltage VP is controlled in such a manner that the value Eλ is constant. As a result, as explained with reference FIGS. 9 and 11, measurement is possible even when the temperature of the solid electrolyte is low (about 600° C.) and the internal resistance is comparatively large. The required power of the heater can thus be reduced on the one hand, and the service life of the sensor is improved on the other hand. The supply current $I_P$ may be controlled instead of the excitation voltage $V_P$.

(3) Also, as explained with reference to FIG. 12, since the excitation voltage is subjected to variations and therefore the output gain remains unchanged with the increase in air-fuel ratio, the supply current $I_P$ may alternatively be controlled as mentioned above.

(4) The solid electrolyte, if used for long time in the rich-mixture region, gains the electron conductivity and the output characteristic thereof develops a hysteresis. In such a case, the electron conduction is prevented in the time-sharing type by reducing the current flowing in the solid electrolyte to zero.

(5) The temperature of the solid electrolyte is kept constant and the detection accuracy improved by controlling the energization of the heater by use of the internal resistance value of the solid electrolyte.

It will thus be understood from the foregoing description that according to the present invention, the air-fuel ratio can be detected over a wide range from lean-mixture to rich-mixture ranges.

We claim:

1. An air-fuel ratio detection system for measuring the air-fuel ratio of a gas mixture burned to produce an exhaust gas, comprising:
   a solid electrolyte;
   first and second electrodes formed on the surface of said solid electrolyte;
   means for passing jump currents through said solid electrolyte between said first and second electrodes;
   said first electrode being exposed to atmospheric air and said second electrode being exposed to the exhaust gas;
   a diffusion resistor formed on said second electrode for controlling exhaust gas diffusion toward said first electrode;
   detector circuit means connected to said first and second electrodes for detecting the conditions of the engine exhaust gas and generating an air-fuel ratio signal therefrom, wherein said detector circuit means further controls said pump currents passing means for changing pump currents between said first and second electrodes to zero during a first period of time and measuring an electromotive force generated between said first and second electrodes during said first period of time; and
   said detector circuit means further including means for controlling said pump currents passing means including means for apply a voltage between said first and second electrodes during a second period of time to keep the electromotive force constant, and means responsive to said pump currents for generating an output signal representing the air-fuel ratio.

2. An air-fuel ratio detection system according to claim 1 wherein said detector circuit means includes sample-hold circuit means operated during said first period for sampling and holding the electromotive force measured, and circuit means for comparing the output of said sample-hold circuit with a reference value and for generating an integrated output on the basis of the difference therebetween during said second period for controlling the voltage between said first and second electrodes.

3. An air-fuel ratio detection system according to claim 1, further comprising:
   said air-fuel ratio detection system having a circuit ground; and
   means for maintaining said second electrode at a potential ground higher in potential than said circuit ground.

4. An air-fuel ratio detection system according to claim 3, further comprising:
   means for heating the solid electrolyte; and
   means for detecting the internal resistance of the solid electrolyte and controlling energization of the heating means to maintain the internal resistance thereof constant.

5. An air-fuel ratio detection system according to claim 4, wherein said means for detecting the internal resistance of the solid electrolyte includes a resistor connected between said second electrode and said maintaining means; and
   means for receiving the potential values of said first and second electrodes the resistance value of said current detecting resistor, and the measured values of the electromotive force such that the detecting of the resistance of said solid electrolyte is on the basis of said values.

6. An air-fuel ratio detection system according to claim 5, wherein said means for receiving of said means for detecting the internal resistance of said solid electrolyte receives the potential of the potential ground in addition to the potential of the second electrode as said potential values of said electrodes.

7. An air-fuel ratio detection system according to claim 4, further comprising:

said means for maintaining said second electrode at a potential ground higher in potential than said circuit ground being a constant voltage source; and said means responsive to said pump currents for generating said output signal being a current detecting resistor connected between said second electrode and said constant voltage source for providing a terminal voltage output that is used as said output signal representing the air-fuel ratio.

8. An air-fuel ratio detection system according to claim 3, further comprising:

said means for maintaining said second electrode at a potential ground higher in potential than said circuit ground being a constant voltage source; and said means responsive to said pump currents for generating said output signal being a current detecting resistor connected between said second electrode and said constant voltage source for providing a terminal voltage output that is used as said output signal represented the air-fuel ratio.

9. An air-fuel ratio detection circuit means includes means for suspending intermittently the voltage being controlled between said first and second electrodes on the basis of the air-fuel ratio detected such that the voltage is suspended more frequently when the detected air-fuel ratio indicates a rich-mixture.

10. An air-fuel ratio detection system according to claim 9, further comprising:

means for heating said solid electrolyte;

means for detecting the internal resistance of said solid electrolyte and controlling the energization of said heating means to maintain the internal resistance thereof at a constant value; and said switching means further including means for operating said detector circuit means during a third period of operation wherein said means for detecting detects the internal resistance of said solid electrolyte, while said pump currents and voltage potential are changed to zero.

11. An air-fuel ratio detection system according to claim 9, wherein said detector circuit means includes means for suspending intermittently the voltage controlled between said first and second electrodes on the basis of the air-fuel ratio detected such that the voltage is suspended more frequently when the detected air-fuel ratio indicates a rich-mixture.

12. An air-fuel ratio detection system for measuring the air-fuel ratio of a gas mixture burned to produce an exhaust gas, comprising:

a solid electrolyte;

first and second electrodes formed on the surface of said solid electrolyte;

means for passing pump currents through said solid electrolyte between said first and second electrodes;

said first electrode being exposed to atmospheric air and said second electrode being exposed to the exhaust gas;

a diffusion resistor formed on said second electrode for controlling exhaust gas diffusion toward said first electrode;

detector circuit means connected to said first and second electrodes for detecting the air-fuel ratio from the exhaust gas conditions;

means for switching said detector circuit means between first and second operation periods;

said detector circuit means having means for changing said pump currents to zero while simultaneously measuring an electromotive force generated between said first and second electrodes during said first period, and means for controlling said pump currents passing means including means for applying a voltage potential across said electrodes during said second period to maintain the measured electromotive force at a constant predetermined value, and means for detecting and outputting a signal responsive to said pump currents, said signal representing the air-fuel ratio.

13. An air-fuel ratio detection system according to claim 12, wherein said detector circuit said first period for sample-hold circuit means operated during said first period for sampling and holding the electromotive force measured, and circuit means for comparing the output of said sample-hold circuit with a reference value and for generating an integrated output on the basis of the difference therebetween during said second period for controlling the voltage potential.

14. An air-fuel ratio detection system according to claim 13, further comprising:

said air-fuel ratio detection system having a circuit ground; and means for maintaining said second electrode at a potential ground higher in potential than said circuit ground.

15. An air-fuel ratio detection system according to claim 14, further comprising:

said means for maintaining said second electrode at a potential ground higher in potential than said circuit ground of said system is a constant voltage source; and said detection and outputting means being a current detecting resistor connected between said second electrode and said constant voltage source for providing a terminal voltage output that is used as said signal representing the air-fuel ratio.

16. An air-fuel ratio detection system according to claim 12, further comprising a microprocessing unit for controlling said switching means.

17. An air-fuel ratio detection system for measuring the air-fuel ratio of a gas mixture burned to produce an exhaust gas, comprising:

a single solid electrolyte cell having only first and second electrodes formed on a surface of said cell;

means for passing pump currents through said cell between said first and second electrodes;

said first electrode being exposed to atmospheric air and said second electrode being exposed to the exhaust gas;

a diffusion resistor formed on said second electrode for controlling exhaust gas diffusion toward said first electrode;

means for measuring an electromotive force generated in said cell;

detector circuit means having a circuit ground connected to said electromotive force measuring means, said pump currents passing means, and said first and second electrodes;

means for switching said detector circuit means between first and second operation periods;

said detector circuit means including means for controlling said electromotive force measuring means to measure the electromotive force of said cell during said first period of time, and said detector circuit means further including means for controlling said pump currents passing means including means for applying a voltage between said first and second electrodes during said second period of time to keep the measured electromotive force constant;

means for maintaining said second electrode at a potential ground higher in potential than said circuit ground; and means connected between said second electrode and said maintaining means for detecting and outputting a signal responsive to said pump currents, said signal representing the air-fuel ratio.

18. An air-fuel ratio detection system according to claim 17, further comprising:

said electromotive force measuring means including said detector circuit means having means for controlling said pump currents passing means to change said pump currents between said first and second electrodes to zero during said first period of time and further including means for measuring the electromotive force between said first and second electrodes during said first period of time.

19. An air-fuel ratio system according to claim 18, wherein said detecting and outputting means is a current detecting resistor connected between said second electrode and said constant voltage source for providing a terminal voltage output that is used as said signal representing the air-fuel ratio.

20. An air-fuel ratio system according to claim 17 wherein said detecting and outputting means is a current detecting resistor connected between said second electrode and said constant voltage source for providing a terminal voltage output that is used as said signal representing the air-fuel ratio.

21. An air-fuel ratio detection system according to claim 17, further including means for heating said solid electrolyte cell;

means for detecting the internal resistance of said cell and controlling the energization of said heating means to maintain the internal resistance thereof at a constant value; and said switching means further including means for operating said detector circuit means during a third period of operation wherein said means for detecting the internal resistance of said solid electrolyte detects the internal resistance of said solid electrolyte while said pump currents and voltage potential are changed to zero.

* * * * *